(12) United States Patent
Blick

(10) Patent No.: US 8,274,059 B2
(45) Date of Patent: Sep. 25, 2012

(54) MOLECULE MASS DETECTION VIA FIELD EMISSION OF ELECTRONS FROM MEMBRANES

(75) Inventor: Robert H. Blick, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 573 days.

(21) Appl. No.: 12/489,037

(22) Filed: Jun. 22, 2009

(65) Prior Publication Data

US 2010/0320372 A1 Dec. 23, 2010

(51) Int. Cl.
*G01T 1/00* (2006.01)
(52) U.S. Cl. .............. 250/397; 250/472.1; 250/473.1; 250/486.1; 250/488.1
(58) Field of Classification Search .............. 250/251, 250/281, 282, 397, 423 P, 423 F, 472.1, 473.1, 250/486.1, 488.1
See application file for complete search history.

(56) References Cited

U.S. PATENT DOCUMENTS

| | | | |
|---|---|---|---|
| 4,060,823 | A | 11/1977 | Howorth et al. |
| 5,994,694 | A | 11/1999 | Frank et al. |
| 6,734,087 | B2 | 5/2004 | Hidaka et al. |
| 7,388,201 | B2 | 6/2008 | Cholewa et al. |
| 7,408,147 | B2 | 8/2008 | Blick et al. |
| 2006/0214257 | A1 | 9/2006 | Ninomiya et al. |
| 2007/0023621 | A1* | 2/2007 | Blick et al. ............ 250/251 |
| 2008/0038894 | A1* | 2/2008 | Rueger et al. ........... 438/308 |
| 2008/0271778 | A1* | 11/2008 | Defries et al. ........... 136/252 |
| 2009/0014757 | A1* | 1/2009 | Takulapalli et al. ........ 257/253 |
| 2009/0092862 | A1* | 4/2009 | Morris et al. ............ 429/9 |

FOREIGN PATENT DOCUMENTS

| | | |
|---|---|---|
| WO | WO 96/04676 | 2/1996 |
| WO | WO 2007/094817 | 8/2007 |

OTHER PUBLICATIONS

Ashcroft, A.E., *Protein and peptide identification: the role of mass spectrometry in proteomics*. Natural Product Reports, 2003. 20(2):202-215.
Coon et al., *Tandem mass spectrometry for peptide and protein sequence analysis*. Biotechniques, 2005. 38(4): 519, 521, 523.
Domon et al., *Review—Mass spectrometry and protein analysis*. Science, 2006. 312(5771): 212-217.
Mann et al., *Analysis of proteins and proteomes by mass spectrometry*. Annual Review of Biochemistry, 2001. 70:437-473.
Twerenbold et al., *Detection of Single Macromolecules Using a Cryogenic Particle Detector Coupled to a Biopolymer Mass Spectrometer*. Applied Physics Letters. 68 (1996) 3503.

* cited by examiner

*Primary Examiner* — David A Vanore
*Assistant Examiner* — Nicole Ippolito
(74) *Attorney, Agent, or Firm* — Greenlee Sullivan P.C.

(57) ABSTRACT

An active detector and methods for detecting molecules, including large molecules such as proteins and oligonucleotides, at or near room temperature based on the generation of electrons via field emission (FE) and/or secondary electron emission (SEE). The detector comprises a semiconductor membrane having an external surface that is contacted by one or more molecules, and an internal surface having a thin metallic layer or other type of electron emitting layer. The kinetic energy of molecules contacting the semiconductor membrane is transferred through the membrane and induces the emission of electrons from the emitting layer. An electron detector, which optionally includes means for electron amplification, is positioned to detect the emitted electrons.

27 Claims, 12 Drawing Sheets

MOLECULE MASS DETECTION VIA FIELD EMISSION OF ELECTRONS FROM MEMBRANES

STATEMENT REGARDING FEDERALLY SPONSORED RESEARCH OR DEVELOPMENT

This invention was made with United States governmental support awarded by the following agencies: USAF/AFOSR FA9550-08-1-0337. The United States government has certain rights in this invention.

BACKGROUND OF THE INVENTION

Over the last several decades, mass spectrometry has emerged as one of the most broadly applicable analytical tools for the detection and characterization of wide classes of molecules. Mass spectrometric analysis is applicable to almost any chemical species capable of forming an ion in the gas phase, and therefore, provides perhaps the most universally applicable method of quantitative analysis. An increased amount of focus has been placed on developing mass spectrometric methods for analyzing complex mixtures of biomolecules, such as peptides, proteins, oligonucleotides, and complexes thereof. In particular, protein sequence analysis has been propelled by advances in the field of mass spectrometry (Domon et al., *Review—Mass spectrometry and protein analysis*. Science, 2006. 312(5771): 212-217; Ashcroft, A. E., *Protein and peptide identification: the role of mass spectrometry in proteomics*, Natural Product Reports, 2003. 20(2): 202-215; Mann et al., *Analysis of proteins and proteomes by mass spectrometry*. Annual Review of Biochemistry, 2001. 70:437-473; and Coon et al., *Tandem mass spectrometry for peptide and protein sequence analysis*. Biotechniques, 2005. 38(4): 519, 521, 523).

Currently, analysis of proteins can be performed by a variety of electrophoresis techniques or by mass spectroscopy. Mass spectroscopy analysis is intrinsically faster and more accurate for the determination of molecular weight. In contrast to electrophoretic mobility, which is an extrinsic and highly condition-dependent property of molecules, the mass to charge ratio (m/z) utilized in mass spectroscopy is an intrinsic and condition-independent property of ions. This means that an m/z ratio determined on a mass spectrometer is intrinsically more accurate and dependable a parameter to employ for the analysis of a molecule than is the electrophoretic mobility. Second, the speed of mass spectroscopy analyses is truly phenomenal, with the potential for milliseconds per analysis. That means that, if mass spectroscopy methods for proteomics can be developed in a suitably robust and high-performance form, they have the potential to radically transform the nature of large-scale sequencing efforts.

A fundamental obstacle in mass spectroscopy has been the limited mass range accessible for the analysis of nucleic acids and proteins using Matrix-Assisted-Laser-Desorption-and-Ionization (MALDI) or Electrospray-Ionization (ESI). This limitation is manifested as a dramatic fall-off in the signal intensity with increasing mass. This phenomenon has limited the analysis of sequencing mixtures to fragment masses of less than 100 kDa, with 50 kDa being more typical. It has been shown that the fall-off in signal intensity for mixtures of large proteins is solely due to instrument-related effects, and not due to chemical issues such as ionization efficiency, or solution or gas-phase fragmentation. A thorough quantitative analysis of the instrumental issues shows that by far the most significant instrumentation issue is ion detection. A combination of the well-known decrease in secondary electron yield from mnicrochannel or electron multiplier detectors with increasing ion mass, as well as the well-known effects of detector saturation in mixture analysis, combine to give the dramatic signal fall-off observed in the mass analysis of these complex mixtures of high molecular weight species.

Currently, among the most sensitive detectors are cryogenic calorimeters, made from superconducting junctions operating at ultra-low temperatures such as less than 100 mK (U.S. Pat. No. 5,994,694; and Twerenbold et al., *Detection of Single Macromolecules Using a Cryogenic Particle Detector Coupled To A Biopolymer Mass Spectrometer*. Applied Physics Letters, 68 (1996) 3503). The superconducting junction is commonly voltage-biased at its steep transition edge of the IV-characteristic, while the crystal is kept at a temperature well below the superconducting transition temperature Tc. Accelerated proteins induce showers of thermal phonons, which heat the whole crystal. This increase in temperature is monitored in the change of the IV-characteristic, since the superconducting phase transition is strongly temperature dependent. The amount of heat deposited by the phonons is directly proportional to the energy of the impinging particles. Thus these superconducting detectors possess an extremely high resolution and are able to resolve even very heavy proteins (several MDa). However, the main drawbacks of this class of detectors are the operating temperatures far below 1K and the limited number of detector pixels (maximal 16). These limitations also include slow recovery time and the fact that the individual detector elements are poorly amenable to arraying due to the complexity, i.e. number of wires to each pixel, and the need to dissipate the heat deposited into the bolometer by the molecular ions. However, even with the current progress being made, it is doubtful that such detectors will ever be operational at or close to room temperature, since they require superconducting elements. The need for cryogenic cooling increases the expense and difficulty of an experiment and is not likely to be readily adopted.

What is needed are detectors able to detect molecules that (1) are as sensitive as possible with unity detection efficiency ('single proton resolution'), (2) do not exhibit a loss in sensitivity for large molecules, and (3) do not require cryogenic temperatures for operation. As resolution continues to be of paramount importance, it is also important that the detectors are fast, so that the process is not detector-limited in resolution.

SUMMARY OF THE INVENTION

The present invention provides an active detector and methods for detecting molecules including proteins and oligonucleotides based on the generation of electrons via field emission (FE) and/or secondary electron emission (SEE) via phonons. The detector comprises a semiconductor membrane having an external surface that is contacted by one or more molecules, and an internal surface having a thin electron emitting layer. The kinetic energy of molecules contacting the semiconductor membrane is transferred through the membrane via the generation of vibrational quanta (i.e. phonons), which travel from the external surface of the membrane to the electron emitting layer on the internal surface and induces the emission of electrons from the emitting layer. An electron detector, which may or may not include a means for electron amplification, is positioned to detect the emitted electrons.

Optionally, the detector is part of a mass spectrometer or a differential mobility analyzer. For example, in one embodiment the detector is mounted in a MALDI/TOF-system for conventional mass spectroscopy and utilizes a multi channel plate (MCP) for signal amplification. Molecules are desorbed and ionized according to the MALDI method and accelerated in a beam line (TOF setup), which subsequently hit the external surface of the membrane. The kinetic energy of the molecule is transferred to the semiconductor membrane and induces emission of electrons from the thin emitting layer. The emitted electrons are detected or amplified using an MCP which provides a signal for mass/electric charge analysis and subsequent sample identification.

In one embodiment, the molecule detector comprises a semiconductor membrane having an external surface for receiving molecules and an internal surface positioned opposite to the external surface, wherein the semiconductor membrane has a thickness of 5 nanometers to 50 microns. Preferably, the semiconductor membrane has a thickness of 10 nanometers to 50 microns, 10 nanometers to 500 nanometers, or more preferably 50 nanometers to 300 nanometers. An electron emitting layer is provided on the internal surface of the semiconductor membrane, wherein the emitting layer has a thickness of 5 nanometers to 10 microns, and wherein the emitting layer emits electrons when the semiconductor membrane receives the molecules. Preferably, the electron emitting layer has a thickness of 10 nanometers to 10 microns, 5 nanometers to 25 nanometers, or more preferably 10 nanometers to 20 nanometers. The molecule detector also comprises an electron detector positioned to detect at least a portion of the electrons emitted by the emitting layer.

The electron emitting layer can comprise any material able to emit electrons via field emission (FE) and/or secondary electron emission (SEE). In one embodiment, the electron emitting layer comprises a material selected from the group consisting of metals, highly doped semiconductors and doped diamond materials. Highly doped diamond materials can be made from diamond-on-insulator (SOI) materials as known in the art. If the electron emitting layer is a thin metallic layer, it is preferable to use a metal that will not oxidize such as gold. The emitting layer conformally coats at least a portion of the internal surface of said semiconductor membrane, preferably between 50% and 100% of the internal surface of the semiconductor membrane.

Optionally, the electron emitting layer is electrically biased so as to generate field emission, secondary electron emission or both. Preferably, the emitting layer is electrically biased by applying a voltage of −3000 V to 3000 V to the emitting layer. The external surface of the semiconductor membrane is also optionally electrically biased by applying a voltage of −2000 V to 2000 V. Alternatively, the semiconductor membrane is provided substantially at ground. The detector may also comprise an electrode positioned between the semiconductor membrane and the electron detector. The electrode is electrically biased so as to generate field emission, secondary emission, or both, from the electron emitting layer or to generate deep emission from the semiconductor membrane itself. In one embodiment, the electrode is a grid electrode which is at least partially transmissive to incident electrons from the electron emitting layer. For example, the grid electrode is able to transmit at least 50% of the incident electrons. Preferably, the electrode is electrically biased by applying a voltage of −2000 V to 2000 V.

The semiconductor membrane comprises one or more layers of a semiconductor material capable of transmitting ballistic phonons and non-ballistic optical and acoustical phonons with traverse or longitudinal, or both, polarizations that are generated when the external surface of the membrane is impacted by a molecule. Preferably, the semiconductor membrane is able to achieve a high conversion efficiency of kinetic energy from molecules contacting the semiconductor membrane to phonons and transmission efficiency of phonons to the electron emitting layer. Conversion efficiency and transmission efficiency can be improved by increasing the hardness and/or Debye temperature ($\Theta_D$) of the semiconductor material. Semiconductor materials suitable for use in the present invention include, but are not limited to, silicon (Si), germanium, (Ge), and silicon nitride (SiN), diamond-on-insulator semiconductors, and combinations thereof. In one embodiment, the semiconductor membrane comprises a plurality of layers of one or more semiconductor materials, wherein each of the layers has a thickness of 1 nanometer to 1000 nanometers. Additionally, the semiconductor membrane may comprise an alternating sequence of layers comprising the same or different semiconductor materials, wherein the sequence comprises two or more layers. In one embodiment, each layer of the semiconductor membrane comprises a single crystalline material. Optionally, the semiconductor membrane further comprises a protective layer provided on the external surface. The protective layer is preferably a thin metallic layer having a thickness of 5 nanometers to 25 nanometers that prevents charging effects of low-conductivity semiconductor materials such as SiN.

In one embodiment, the emitting layer and internal surface of the semiconductor membrane are substantially flat without any protrusions, such as relief features having longitudinal dimensions of 100 nanometers or greater. However, using sputtering techniques to add an emitting layer, such as a metal layer, to the semiconductor membrane will result in small spikes or areas of surface roughness being formed on the emitting layer as compared to a very smooth surface. These spikes and surface roughness may reduce the voltage threshold due to geometrical reduction factor and may enhance the emission probability. In one embodiment, the emitting layer has a uniform thickness that does not vary by more than 20% over an active area, preferably by no more than 10%, even more preferably by no more than 5%. In a further embodiment, the combined thickness of the semiconductor membrane and emitting layer has a uniform thickness that does not vary by more than 20% over an active area, preferably by no more than 10%, even more preferably by no more than 5%.

U.S. Pat. No. 7,408,147 discloses devices and methods for detecting molecules in MALDI, ESI and TOF systems utilizing nanopillars having lengths between approximately 100 nanometers and 3 microns attached to the inner surface of a membrane impacted by the molecules. While the present invention may be able to accommodate the use of nanopillars, the present invention does not require nanopillars for successful generation or propagation of phonons or emission of electrons. In certain embodiments of the present invention, the detector does not contain any nanopillars or similar structures attached to the semiconductor membrane. It is understood that nanopillars are meant to be excluded from these embodiments.

The generation and propagation of phonons is more efficient at extremely low temperatures. Low temperatures, such as below 100 Kelvin, reduce the amount of electrical background noise and reduce the amount of energy lost due to conversion to thermal energy, although it should be noted that application of large voltages for electron extraction and electron emission can lead to heating of the semiconductor membrane. However, maintaining such low temperatures is costly and requires great effort. While the detector of present invention would be functional at cryogenic temperatures, the semiconductor membrane is capable of converting the phonon energy into FE and/or SEE at room temperature and above room temperature. Preferably, the detector is provided at a temperature between 10 mK and 1500 K, more preferably between 2 K and 600 K, even more preferably between 250 K and 400 K. The upper operating temperature is dependent on the disintegration temperature of the semiconductor material (approximately 1700 K for Si).

The electron detector can be any device known in the art able to receive and detect electrons emitted from the emitting layer. The electron detector may optionally comprise means for amplifying electrons emitted from the emnitting layer, including but not limited to an oscilloscope. In one embodiment, the electron detector comprises one or more microchannel plates (MCP) or dynodes positioned in the path of electrons emitted by the emitting layer. In another embodiment, the electron detector further comprises a photoluminescent screen and photodetector, wherein the photoluminescent screen receives electrons emitted by the emitting layer and generates electromagnetic radiation which is detected by the photodetector. Preferably, the electron detector is positioned 50 nanometers to 10 centimeters from the electron emitting layer. Alternatively, the MCP and membrane are combined, which reduces background drift and noise, while increasing the detectable mass range. This is based on the energy transduction mechanism of the membrane, as it converts most of the kinetic energy first into lattice vibrations within the membrane and then into emitted electrons. The emitted electrons are then further multiplied by the MCP.

Optionally, the detectors of the present invention comprise a substrate having one or more active detector areas able to receive a molecule, where each active detector area comprises a semiconductor membrane and emitting layer. The semiconductor membrane for each active area can be selected or manipulated to be sensitive for a specific molecule mass. The active areas of the detector can be made sensitive to the same molecular mass or different molecular masses compared to one another. Preferably, each active area has a surface area between 0.1 millimeters$^2$ to 20$^2$ centimeters$^2$. Alternatively, each active area can have a surface area smaller than 0.1 millimeters$^2$ but form a total area greater than several square inches.

Another embodiment of the present invention provides a method of detecting a molecule by providing a detector comprising: a) a semiconductor membrane having an external surface for receiving molecules, and an internal surface positioned opposite to the external surface, wherein the semiconductor membrane has a of 5 nanometers to 50 microns, and b) an electron emitting layer comprising a material selected from the group consisting of metals, doped semiconductors and doped diamond materials provided on the internal surface of the semiconductor membrane, wherein the emitting layer has a thickness of 5 nanometers to 10 microns, and wherein the emitting layer emits electrons when the semiconductor membrane receives molecules. The method further comprises contacting molecules with the external surface of the membrane, thereby generating electrons emitted by the emitting layer; and detecting the electrons emitted by the emitting layer. In a further embodiment, detecting the emitted electrons comprises positioning an electron detector in the path of at least a portion of the emitted electrons and optionally amplifying the emitted electrons using a MCP or dynode. Optionally, the emitting layer, semiconductor layer or both are electrically biased. The emitting layer is electrically biased so as to establish an electric potential across the emitting layer of −3,000 V to 3,000 V.

Another embodiment provides a method of detecting molecules comprising the steps of:

a) providing a detector having active detector areas, wherein each active detector area comprises: a semiconductor membrane having an external surface for receiving molecules, and an internal surface positioned opposite to the external surface, wherein said semiconductor membrane has a thickness of 10 nanometers to 50 microns; an electron emitting layer comprising a material selected from the group consisting of metals, doped semiconductors and doped diamond materials provided on the internal surface of the semiconductor membrane, wherein the emitting layer has a thickness of 5 nanometers to 10 microns, and wherein the emitting layer emits electrons when the semiconductor membrane receives molecules;

b) contacting molecules with the external surface of said semiconductor membrane;

c) converting the kinetic energy of molecules contacting the external surface into lattice vibrations of the semiconductor membrane to generate phonons;

d) transferring the phonons to the emitting layer, thereby generating electrons from the emitting layer in response to the transfer of phonons; and e) detecting electrons emitted by the emitting layer.

Molecules able to be detected using the detector and methods of the present invention include large molecules (at least 50 kDa, at least 100 kDa or even at least 1,000 kDa) such as proteins and oligonucleotides. Because the detector utilizes the kinetic energy of the molecule contacting the semiconductor membrane to generate phonons, the present invention is able to detect neutral molecules, which are not charged or are difficult to ionize with traditional MALDI techniques, thereby enabling a broad range of highly-sensitive molecule detection schemes for proteomics. Thermal and/or electrical manipulation of the molecules and the membrane can be used to further enhance detection of neutral molecules. The detector is compatible with existing technology while enabling the detection of neutral molecules and large proteins, which cannot be done effectively with existing technology.

In one embodiment, the detectors of the present invention may also have energy detection functionality. For example, the detectors of the present invention may be used to measure the kinetic energy of a molecule impacting the external surface of the detector. The energy and the number of phonons generated upon impact of the molecule is directly proportional to the kinetic energy of the molecule. Consequently, the number of electrons emitted from the membrane is also proportional to this energy. An integration over the peak area then delivers this total kinetic energy of the incoming particles.

The detector of the present invention provides a versatile detection platform for a range of mass analyzers, including but not limited to quadrupole mass analyzers, magnetic sector mass analyzers, time of flight mass analyzers, and ion trap mass analyzers.

In one embodiment, the molecules detected by the detector of the present invention are ions. The ions impact the external surface of the membrane with a kinetic energy of 10 keV to 50 keV. The kinetic energy of the ions is at least partially converted into lattice vibrations of the semiconductor membrane. In a further embodiment, the detector comprises a time of flight analyzer in fluid communication with the external surface of the semiconductor membrane. Ions separated by the time of flight analyzer impact the external surface of the semiconductor membrane allowing time of flight data to be collected with the detection of the molecules. In another embodiment, the detector comprises an ion accelerator in fluid communication with the external surface of the semiconductor membrane, where ions are accelerated by the ion accelerator and impact the external surface of the semiconductor membrane.

A further embodiment of the present invention comprises means for releasing molecules that have contacted the external surface of the semiconductor membrane. Means for releasing molecules from the external surface includes, but is not limited to, generating a pulse of thermal energy, a pulse of electromagnetic radiation, a pulse of electric current or a shock wave on the external surface of the semiconductor membrane.

DETAILED DESCRIPTION OF THE INVENTION

Definitions

Figure 1:
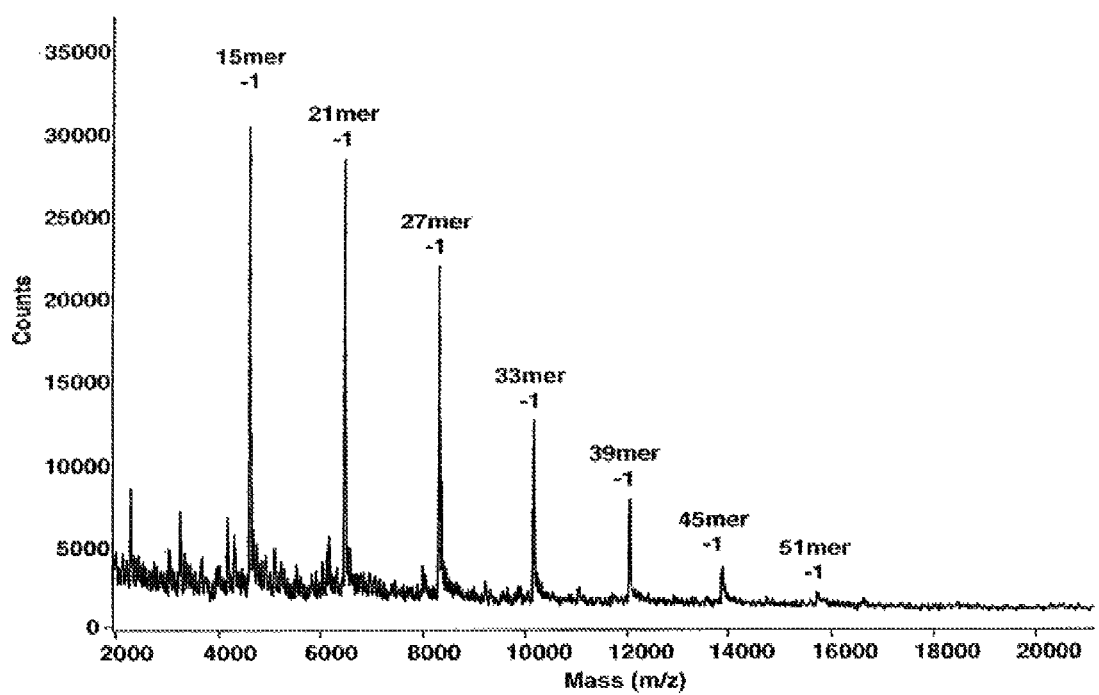
FIG. 1 shows a representative mass spectrum of an equimolar mixture of oligonucleotide standards using standard instruments. The spectrum illustrates signal fall-off associated with increasing mass of the detected molecules.

"Molecule" refers to a collection of chemically bound atoms with a characteristic composition. As used herein, a molecule refers to neutral molecules or electrically charged molecules (i.e., ions). Molecules may refer to singly charged molecules and multiply charged molecules. The term molecule includes biomolecules, which are molecules that are produced by an organism or are important to a living organism, including, but not limited to, proteins, peptides, lipids, DNA molecules, RNA molecules, oligonucleotides, carbohydrates, polysaccharides; glycoproteins, lipoproteins, sugars and derivatives, variants and complexes of these.

"Ion" refers generally to multiply or singly charged atoms, molecules, and macromolecules having either positive or negative electric charge and to complexes, aggregates and clusters of atoms, molecules and macromolecules having either positive or negative electric charge. Ion includes cations and anions.

"Membrane" refers to a device component, such as a thin, predominantly flat structural element. Membranes of the present invention include semiconductor membranes able to emit electrons when molecules contact the receiving side of the membrane. Membranes useful in the present invention may comprise a wide range of additional materials including dielectric materials, ceramics, polymeric materials, glasses and metals.

"Field emission" (FE) or "field electron emission" (FEE) is the discharge of electrons from the surface of a condensed material (such as a metal or semiconductor) subjected to a strong electric field into vacuum or into another material.

"Secondary emission" or "secondary electron emission" (SEE) is a phenomenon where primary incident particles of sufficient energy, when hitting a surface or passing through some material, induce the emission of secondary particles, such as electrons.

"Active area" refers to an area of a detector of the present invention that is capable of receiving molecules and converting the kinetic energy of the molecules impacting the surface to generate phonons.

"Phonon" refers to a unit of vibrational energy that arises from oscillating atoms within a crystal lattice.

"Semiconductor" refers to any material that is a material that is an insulator at a very low temperature, but which has an appreciable electrical conductivity at a temperature of about 300 Kelvin. In the present description, use of the term semiconductor is intended to be consistent with use of this term in the art of microelectronics and electrical devices. Semiconductors useful in the present invention may comprise element semiconductors, such as silicon, germanium and doped diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors CuCl, group IV-VI semiconductors such as PbS, PbTe and SnS, layer semiconductors such as Pbl2, MoS2 and GaSe, oxide semiconductors such as CuO and Cu2O. The term semiconductor includes intrinsic semiconductors and extrinsic semiconductors that are doped with one or more selected materials, including semiconductor having p-type doping materials and n-type doping materials, to provide beneficial electrical properties useful for a given application or device. The term semiconductor includes composite materials comprising a mixture of semiconductors and/or dopants.

In the following description, numerous specific details of the devices, device components and methods of the present invention are set forth in order to provide a thorough explanation of the precise nature of the invention. It will be apparent, however, to those of skill in the art that the invention can be practiced without these specific details.

FIG. 1 shows a representative mass spectrum obtained from conventional devices using an equimolar mixture of oligonucleotide standards. The spectrum illustrates a signal fall-off as the molecules increase in mass. Conventional devices are limited to oligonucleotides having less than 100 nucleotides, with 50 nucleotides being the more typical limit. This result is similar with other molecules as mass increases. The present invention utilizes the kinetic energy of the molecules as they impact the surface of the detector, which allows for the detection of large and small molecules. Detectors of the present invention have been used to analyze a wide range of proteins/peptides, including large peptides such as bovine insulin (approximately 5,733 Da), angiotensin (approximately 1,296 Da) and cytochrome C (approximately 12,362 Da) as shown in FIGS. 7-10.

Figure 2:
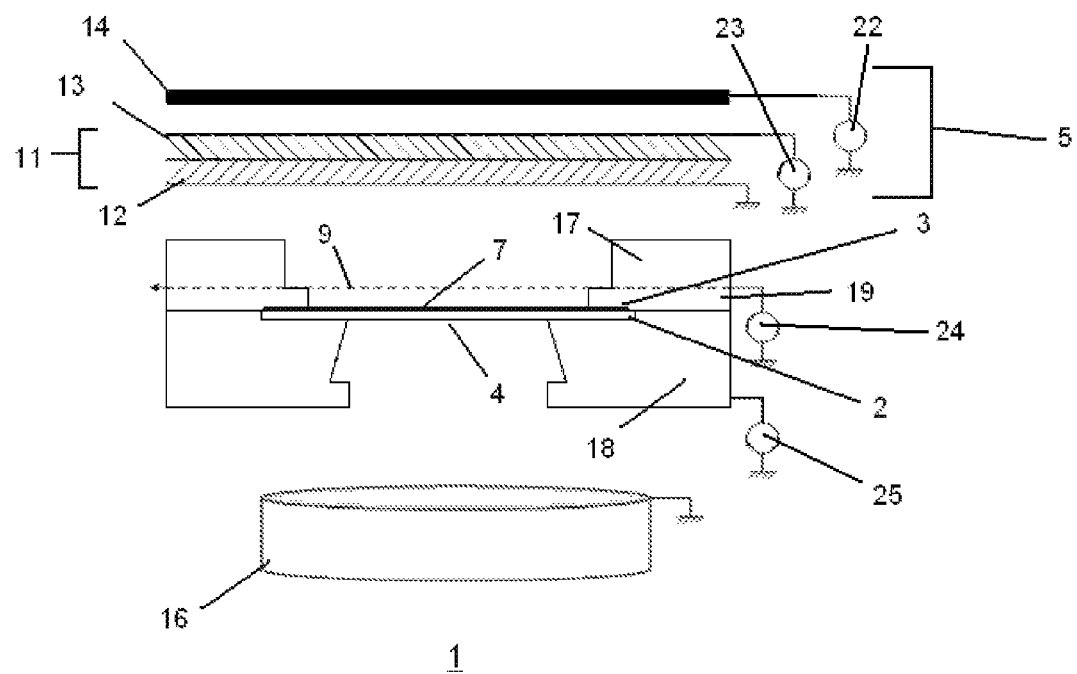
FIG. 2 illustrates a detector of the present invention. A semiconductor membrane with an emitting layer is positioned so that molecules from a flight tube contact the external surface of the semiconductor membrane. Electrons emitted from the emitting layer are transmitted through a grid electrode to an electron detector, which includes a MCP.
Figure 3:
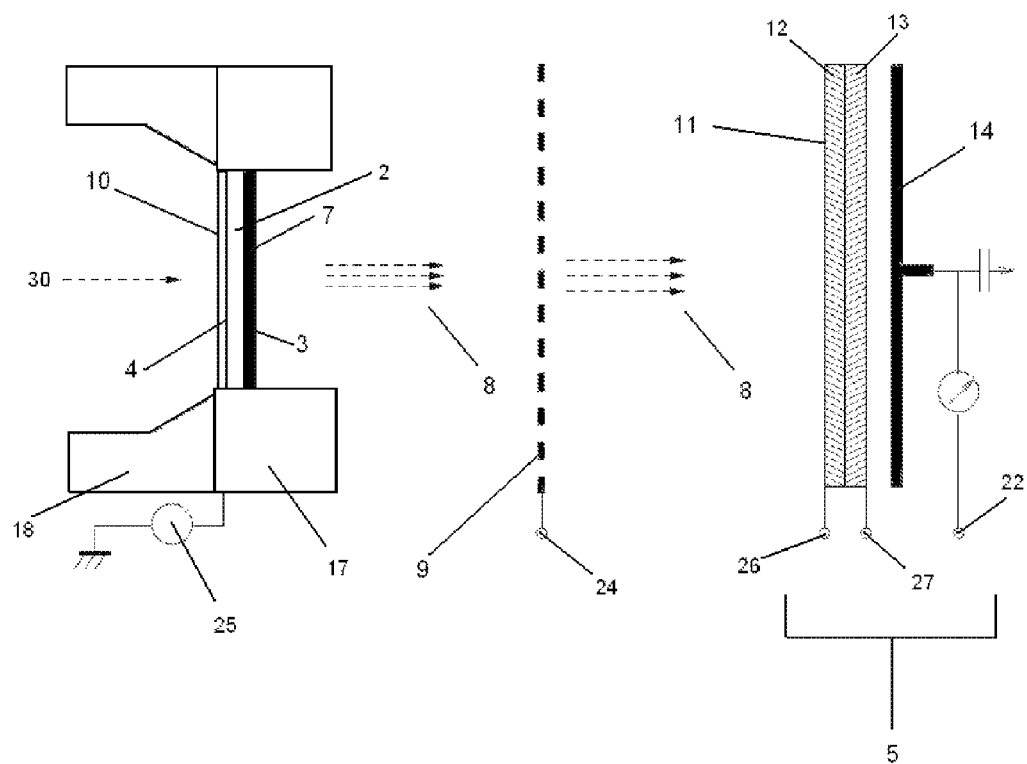
FIG. 3 illustrates a similar detector of the present invention with a metal grid electrode positioned between the semiconductor membrane and electron detector. The path of electrons emitted from the metallic emitting layer is also illustrated.

The basic design and principle of operation of the detectors 1 of the present invention is indicated in FIGS. 2 and 3. A thin semiconductor membrane 2 (preferably 10 nanometers to 300 nanometers in thickness) is machined from a semiconductor structure. The external surface 4 of the membrane 2 is positioned to receive molecules 30 (illustrated in FIG. 3) from a molecule source 16, such as an ion accelerator or flight tube. The internal surface 7 of the semiconductor membrane 2 comprises an electron emitting layer 3 from which electrons 8 (illustrated in FIG. 3) are emitted when a molecule impacts the external surface 4 of the membrane 2. A thin protective layer 10, typically a thin metal layer, may coat the external surface 4 (as shown in FIG. 3). For example, the semiconductor membrane can comprise a 100 nanometer layer of SiNx having a 30 nanometer gold protective layer positioned on the external surface and a 15 nanometer gold layer on the internal surface, where the 15 nanometer layer serves as the electron emitting layer. Emission of electrons stems from the 30 nanometer layer as shown in FIG. 3, i.e. from the external surface according to the notation. The semiconductor membrane 2 is supported by a top detector holder 17 and bottom detector holder 18 and may utilize an inert spacer 19, such as teflon, to position the electrode 9 in close proximity to the emitting layer 3. For example, in one embodiment electrode 9 is a metal grid having approximately 70 LPI (lines per inch) and is held in position by an inert spacer 19 having a thickness of approximately 127 micrometers.

The emission of electrons 8 from the emitting layer 3 is proportional to the strength of the impact, i.e. the transferred momentum and thus the energy of the molecule. The emitted electrons 8 are in turn accelerated by gating electrode 9 and collected by electron detector 5. The electron detector 5 optionally includes a standard multichannel plate (MCP) 11 and an anode 14 which detects the electrons 8. Electrons 8 contact the MCP input layer 12 causing additional electrons to be emitted by the MCP 13 output layer which amplifies the electrons 8. In one embodiment, such as illustrated in FIG. 3, the electrode 9 is positioned approximately 0.5 mm from the top detector holder 17 and 10 mm from the MCP 11. Furthermore, an anode voltage 22, MCP voltage 23, grid voltage 24, and/or detector voltage 25 can be applied to electrically bias the different components. As illustrated in FIG. 3, the MCP 11, can be electrically biased by applying a MCP input layer voltage 26 and/or a MCP output layer voltage 27.

Figure 4:
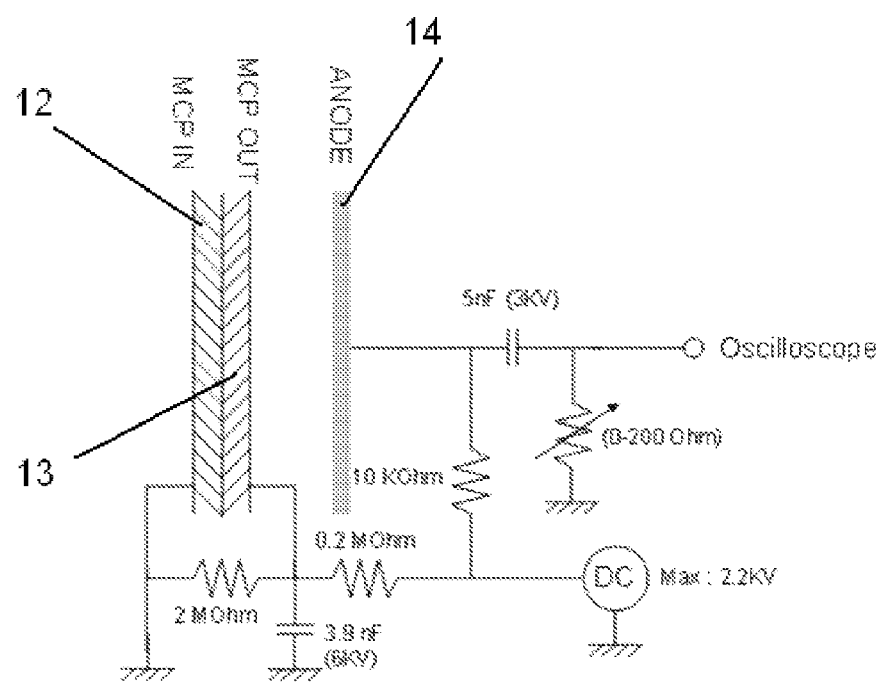
FIG. 4 illustrates the circuitry of an electron detector comprising an MCP used to amplify the electrons, an anode used to collect the electrons and generate a voltage, and an oscilloscope used to measure the voltage.

The anode 14 can be part of an oscilloscope 15 or other device able to detect and display the presence of electrons, such as shown in FIG. 4. The accelerated and charged molecules collide with the semiconductor membrane 2 and their momentum induces electron emission via phonon-assisted tunneling from the emitting layer 3. At this point it should be stressed that the detector is capable of resolving a molecule's mass (m) via direct phonon detection, but can also sample the ionized molecule's charge state or valence (z).

Figure 5:
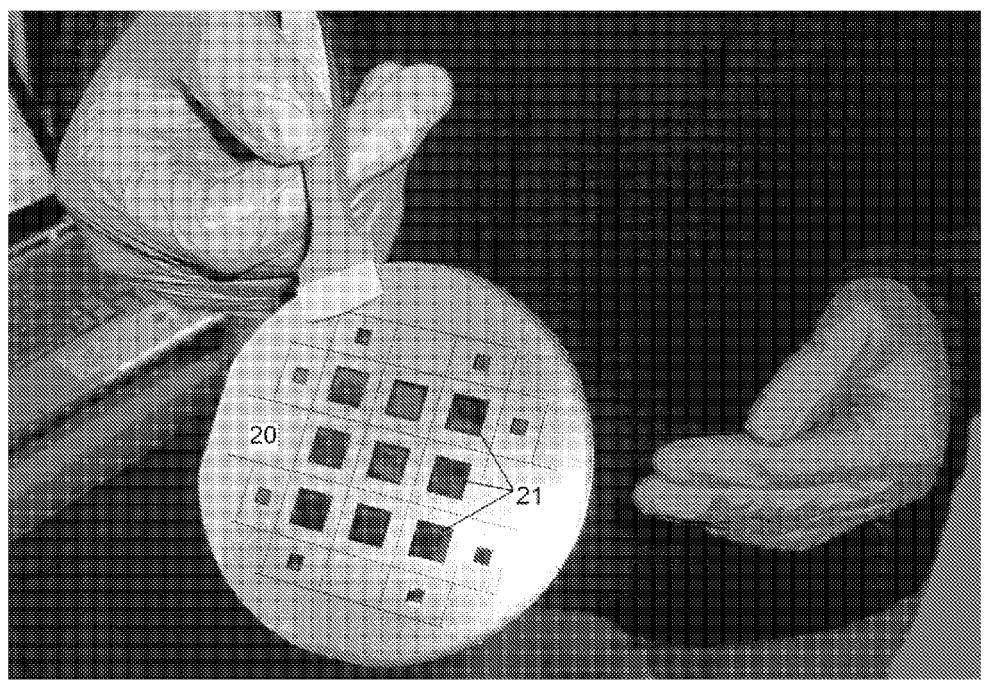
FIG. 5 shows a semiconductor membrane of the present invention on a substrate. Each of the windows is an active detector area, while the silver patterned layers are mechanically supporting the membranes.

A molecule 30, such as a protein, impacts on the external surface 4 of the semiconductor membrane 2 and excites ballistic and non-ballistic phonons. Once the molecule 30 hits the membrane 2, a part of the energy that the molecule acquired will be dissipated into formational changes within the molecule, while about half of it will excite phonons in the membrane. If the molecule is charged, this charge could also be expected to be detected by the detector 1. A detector 1, as shown in FIG. 5, may also comprise a substrate 20 having multiple active areas 21, where each active area 21 has a semiconductor membrane 2 and emitting layer 3.

Figure 6:
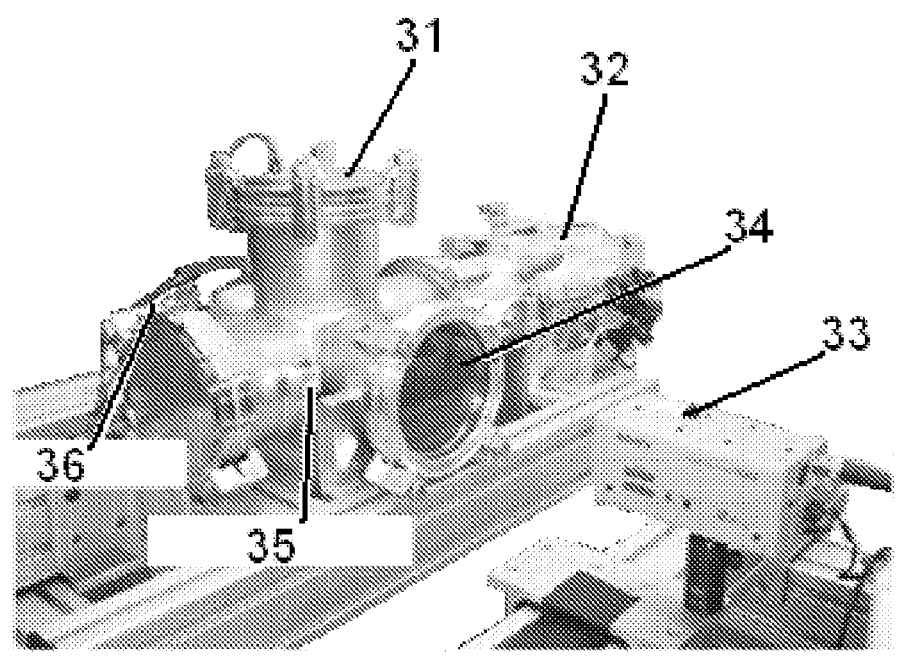
FIG. 6 shows a time of flight/MALDI system incorporating a detector of the present invention.

Preferably, the detector 1 is integrated into a mass spectroscopy system, such as shown in FIG. 6 which depicts an UHV-vacuum chamber 31, a turbo pump 32, a high resolution CCD camera 33, a detector output window 34, detector location 35, and a port for a MALDI/TOF unit 36. There are two primary methods that allow large molecules to be introduced into the vacuum of a mass spectrometer, electrospray ionization (ESI) and matrix-assisted laser desorption/ionization (MALDI). The advantage of MALDI has been the fact that it produces predominantly singly-charged molecular ions of the analyte, and hence is relatively well-suited to mixture analysis (one peak per component, yielding simple and readily interpretable mass spectra). ESI, although a gentler ion production process with generally higher mass accuracy than MALDI, has the property that it produces complex distributions of ions in various charge states, and hence has not generally proven suitable for the analysis of mixtures containing many components (many peaks per component, causing "spectral congestion").

Time-of-flight (TOF) separation is a well-established technique for mass selection and can be used for separation of the proteins. Charged proteins are accelerated in a DC electric voltage of some V=20–30 kV to an energy of $E_{ei}=qV=zeV$ and funneled through an aperture into the TOF-chamber (e is the elementary charge). Within the chamber, mass separation occurs according to the kinetic energy $E_{ei}=E_{kin}=mv^2/2$, which leads to a mass-dependent time of flight of $t=d/v=d(m/2\ qV)^{1/2}=d/(2\ eV)^{1/2}(m/z)^{1/2}=k\ (m/z)^{1/2}$, with d as the distance traveled and $k=d/(2\ eV)^{1/2}$, as the scaling factor. This approach leads to a separation, where the smallest particles come through first, while the largest molecules are the slowest. Depending on the acceleration voltage and TOF-chamber length, the resolution can be enhanced. For mass spectroscopy of large proteins, a TOF-chamber length of about d=1–2 m is sufficient. The mass of the molecule can be obtained by measuring t. In mass spectrometry the resolution is defined as $m/\Delta m$. From the above equation, it can be shown that:

$$\frac{m}{\Delta m} = \frac{t}{2\Delta t}.$$

This simple equation demonstrates that the greater the homogeneity in the arrival times of a particular ion and the more precisely the timing measurement can be made, the greater the ability to resolve its mass from other ions. The quantity to be measured is thus the charge of a particular molecule, which arrives after time t. The typical times one has to work with are on the order of several 1-100 micro-seconds.

The electron detector can be any device known in the art and optionally amplifies the electrons emitted by the semiconductor membrane such as through the use of microchannel plates (MCP). Microchannel plates are made up of a parallel array of miniature channel electron multipliers. Typically, the channel diameters are in the range of 10 to 100 microns with the lengths of the channels in the neighborhood of 1 mm. Each channel operates as a continuous dynode structure, meaning that it acts as its own dynode resistor chain. A potential of 1 to 2 kV is placed across each channel. When an energetic molecule enters the low potential end of the channel and strikes the wall of the channel, it produces secondary electrons, which are in turn accelerated along the tube by the electric field. These electrons then strike the wall, generating more electrons. The process is repeated many times until the secondary electrons emerge from the high potential end of the channel. Generally speaking, for each molecule which initiates a cascade, $10^4$ electrons emerge from the channel, providing significant gain and hence the ability to make the detection of a single molecule possible.

Both discrete and continuous dynode detectors rely on secondary electron emission (SEE) for operation. Secondary emission occurs when a surface, under vacuum, is bombarded by molecules or electrons with energies ranging from 10 to a few 1000 electron volts. For most materials the number of secondary electrons produced by each primary electron lies between 0.2 and 3. This number, which corresponds to the average number of electrons created, is known as the secondary emission coefficient. Typical discrete dynode detectors employ up to 16 stages (dynodes). Total gain from this system can reach $10^8$. The potentials are established on each dynode by a resistive potential divider, or alternatively each dynode may be connected to its own external circuit to provide quick electron replenishing when being used with high repetition rates. The continuous dynode detector, on the other hand, relies on a highly resistive material such that the potential can be placed across the entire device.

For a given class of molecule, an MCP can be very sensitive, with single molecule detection capabilities. It can be made large in area, ideal for analysis of packets of ions as described above. Lastly, they exhibit very fast rise times, on the order of several nanoseconds.

EXAMPLES

Semiconductor membranes of Si and SiN and having a thin layer of gold functioning as the emitting layer were used to form active detectors for proteins and other large molecules. The detectors were mounted in a MALDI/TOF-system for conventional mass spectroscopy and incorporated an MCP (multi channel plate). Molecules are desorbed and ionized (MALDI-method) and accelerated in a beam line (TOF-setup) and contacted with the external surface of the membrane. The kinetic energy $E_{kin}=\frac{1}{2} mv^2$ of the molecule is transferred to the membrane via the generation of vibrational quanta (phonons), which travel from the back to the front. On the front side the vibration energy is again transferred but now to support emission of electrons from the thin emitting layer on top. The metal itself is voltage biased to just below the onset-voltage of conventional field emission. The experiments described below showing ion detection were performed at room temperature unless specifically stated otherwise.

Example 1

Figure 12:
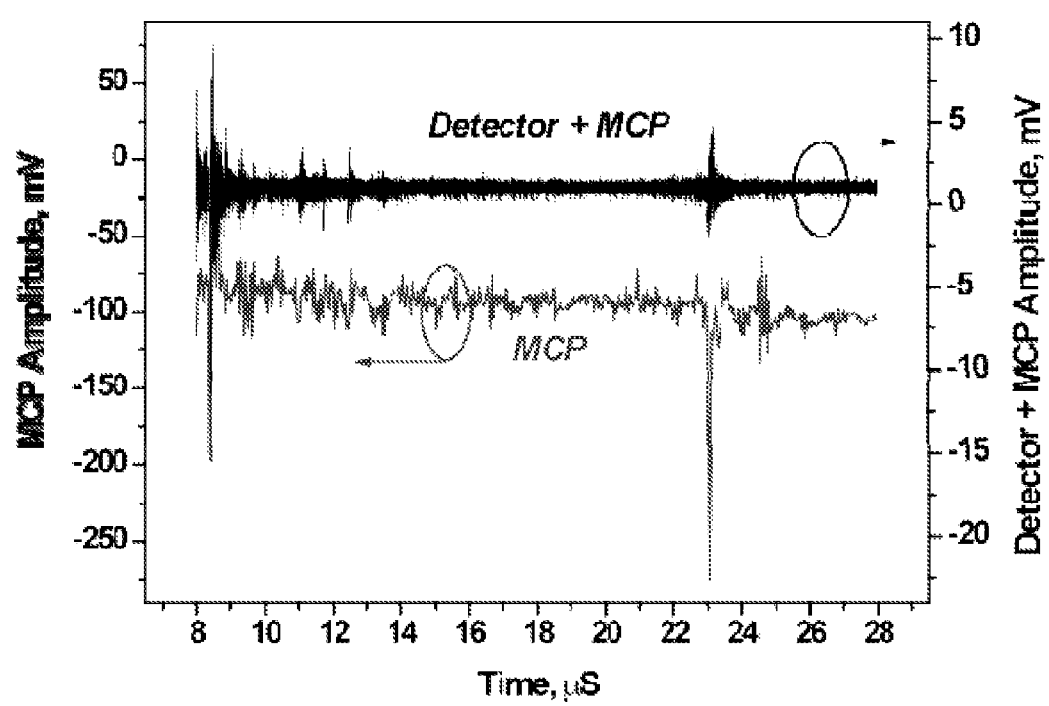
FIG. 12 shows a comparison of a conventional MCP and the combined Membrane-MCP detector of the present invention.

Measurements from the detector of the present invention compared with standard MCP detectors are summarized in FIG. 12. Two data traces are shown, one of the conventional MCP detector (labeled as MCP) and another one using the membrane-detector of the present invention with an MCP (labeled as Detector+MCP). As seen, both detectors find the same peak structure with the most prominent peak around the 23 micro-second mark. This is the peak stemming from the molecule (angiotensin) used as a test sample in this particular case. This molecule is negatively charged and accelerated in the MALDI-TOF unit and then travels for 23 micro-seconds before it impacts on the detector. The smaller peaks appearing at shorter time-scales are the molecules used in the so-called matrix, i.e. the solution in which the angiotensin was prepared.

On closer inspection one finds several remarkable facts apart from the proof-of-concept of the membrane detector itself. First of all, the background drift of the semiconductor membrane detector-MCP system is much lower than the conventional MCP-drift. Second, the noise in for the membrane detector-MCP system is lower than the conventional MCP detector and can still be further improved (biasing condition optimization and field emission tuning). Lastly and most importantly, the mass range of the membrane detector-MCP system is not limited as the MCP detector. This is due to the energy transduction mechanism of the semiconductor membrane. It mainly converts most of the kinetic energy first in lattice vibrations within the membrane and then into 'kicking' electrons over the field emission barrier. The emitted electrons are then further multiplied by the MCP sandwiched to the membrane. As a final note it has to be pointed out that by using thermally excited molecules, i.e. not using a DC electric field to create propagation, the membrane detector-MCP system can also probe so-called neutrals, i.e. molecules which are not charged or are difficult to ionize with MALDI. Obviously the membrane detector-MCP system opens up a broad range of highly-sensitive molecule detection schemes with a possible great impact in the field of protein mass analysis and thus proteomics.

Example 2

The overall detection mechanism can be separated into three different events: (a) impact of the molecule (such as a charged protein), (b) generation of ballistic phonons or non-ballistic phonons (such as acoustical phonons) in the semiconductor membrane, and finally (c) emission of an electron via phonon-assisted-tunneling from the emitting layer. Depending on the biasing conditions and the detailed mechanical and electronic structure of the detector, it is possible to generate not only a single electron but a multitude of electrons, i.e., the device can operate with large gain. The generated electrons were subsequently detected by either a conventional MCP electron detector or a fluorescent screen. The energy of the excited phonons is proportional to the mass and thus the momentum transferred by the molecule. That ensures that the accelerated mass was measured, which is proportional to the impact energy and thus the energy of the excited phonons.

In a straightforward approach, the total energy of the proteins is determined by the energy they acquire in the DC electric field of the MALDI unit. This results in a kinetic energy of the protein of $E=\frac{1}{2}mv^2$, where again m is the mass of the protein and v its final velocity. This gives the maximal amount of energy for a phonon being excited in the detector. The usual acceleration voltages in a MALDI/TOF chamber are on the order of 10 kV, which translates into phonon frequencies of order 3000 PHz. For more moderate acceleration energies on the order of $E_{DC\text{-}field}=1.24$ eV, the possible phonon energy will still be very high, with about $E_{ph}=h\times300$ THz (as usual, h denotes Planck's quantum). The energy supplied by the electric field will be the upper bound for the possible excitations of the detector. The charged molecule impacts the external surface of the membrane with a large energy, large enough to excite ballistic phonons even at room temperature (the thermal energy at room temperature is simply given by $E_{thermal}=k_B T=k_B (300 \text{ K})=26$ meV=h (6 THz), with $k_B$ denoting Boltzmann's constant).

In contrast to classical solid-state detectors such as standard MCP systems, the present detector has remarkable thinness (preferably the semiconductor membrane is between 50 and 300 nanometers). This ensures that the mechanical vibrations (phonons) generated by the impact of a particle, such as an accelerated protein, are not completely thermalized into low-energy phonons as in classical calorimetric detectors, but are preferably transmitted as high energy ballistic phonons (ballistic means they travel without undergoing scattering). The excited phonons with energies of several THz travel through the membrane and subsequently into the emitting layer, where they induce electron emission into vacuum. The assumption of ballistic-phonon propagation is justified for thin enough membranes, since the mean free path of phonons in Si and SiN is on the order of 300 nanometers at room temperature. With a typical impact energy of several tens of eV (corresponding to several 100 THz), there is sufficient energy to excite phonons and the follow-up electrons from the emitting layer.

Example 3

Sample fabrication is based on standard semiconductor processing steps involving optical lithography, doping of the material, and wet and dry etching steps although other processes can also be used. Processing starts from silicon-on-insulator (SOI) wafers. Specially grown wafers were received through collaborators at Soitec Corp. and UW-Madison. The top silicon layers of the 501-wafers were doped or sent to outside sources for high n- and/or p-type doping. In the first sequence of optical lithography, metallic leads were defined and both sides of the wafer prepared for subsequent etching steps. In order to define free-standing membranes made from silicon or silicon-nitride, a KOH-wet etch step was used. This opens windows from the backside of the wafer and only leaves thin to ultrathin membranes.

One example of such a very thin membrane (200 nm) is shown in FIG. 5, where whole wafer processing was applied. As seen the membranes in FIG. 5 (nine squares) are semi-light-transparent. The membrane material itself can currently be made from silicon, silicon-nitride, or silicon-germanium heterostructures (Site). The strain within the membranes was engineered by adjusting the layer thickness and composition of the SiGe-structure. Finally, the top side of the membranes are patterned by a combination of optical and electron beam lithography and dry etching in reactive ion etchers (RIE). Electron beam lithography currently allows features on a 2"-wafer to be defined as small as 30 nanometers.

In addition to using silicon and other group IV elements, membranes can be fabricated from doped diamond-on-SOI starting materials. The apparent advantages of diamond are the extremely low energy required for field emission of electrons and its mechanical strength. This will enable lower operating voltages to be used and increase the membrane size.

Example 4

To test the prototype detector, a MALDI/TOF system was set up as shown in FIG. 6. The system included relevant components as known in the art: vacuum chambers, pumps, laser for MALDI, measurement computer, MCP, fluorescent screen, and a high-resolution CCD camera for readout. The principles of operation of the present detector do not require low temperatures, since the phonon energies to be detected are of order several 10 THz, much larger than the corresponding room temperature energy of $E_{th}=h\times 6$ THz. Nevertheless, a 'cold finger' was integrated in the setup. This unit enables temperatures down to 4 K to be reached. The measurement unit is thus extremely flexible and is able to supply information on the detector performance over a broad temperature range. In addition optical windows are integrated into the TOF-unit of the setup. These windows enable optical access to the semiconductor membrane which support the generation of electrons via illumination with a laser. Another optical port gives access to the back-side of the membrane, allowing the removal of ablated proteins after detection by a laser heat pulse.

In order to carry out the measurements with ionized proteins, traditional MALDI/TOF detection was used, i.e., ionizing the molecules and detecting their impact gauged by the time-of-flight (TOF-mode detector to observe the detection of the molecule's charge). After this, the TOF-mode for phonon detection is used in which the impacting molecule will generate phonons, which in turn cause the emission of electrons. These two methods—charge and mass detection—are then combined and calibrated with the help of equimolar test solutions (larger peptides of known masses). Finally, the 'energy resolution mode' is used, where the number of electrons emitted is proportional to the excited phonon energy and thus to the mass of the molecule.

Figure 7:
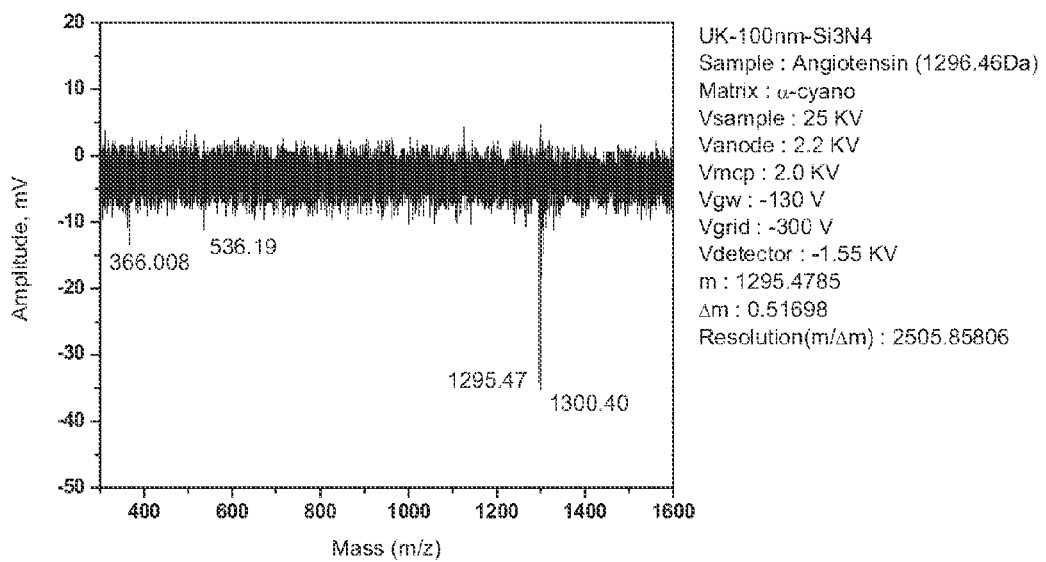
FIG. 7 shows a mass spectrum of angiotensin (1,289 Da) obtained using a detector of the present invention.
Figure 8:
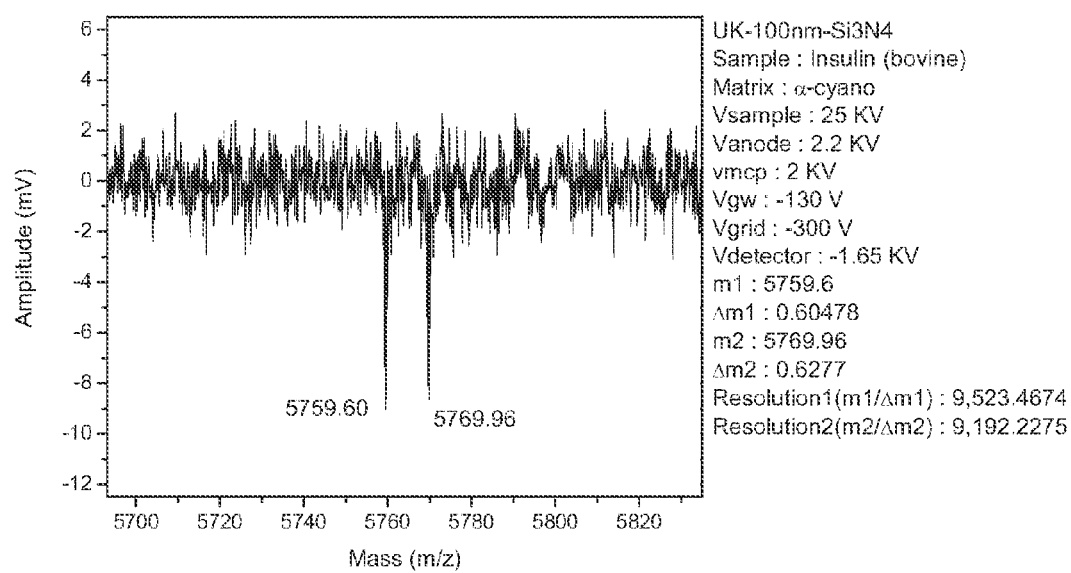
FIGS. 8 and 9 show mass spectra of bovine insulin obtained using detectors of the present invention.
Figure 9:
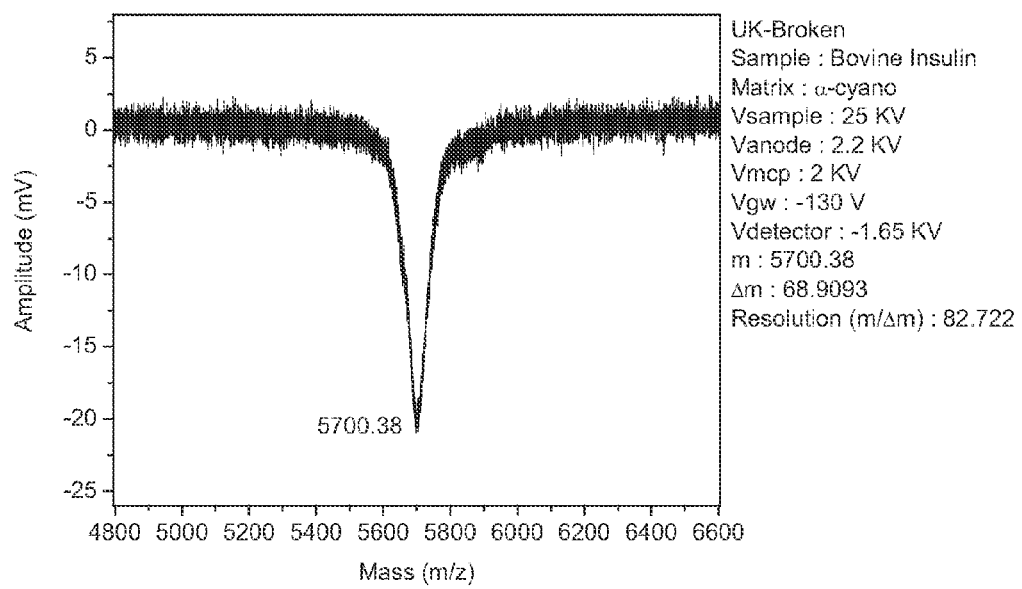
Figure 10:
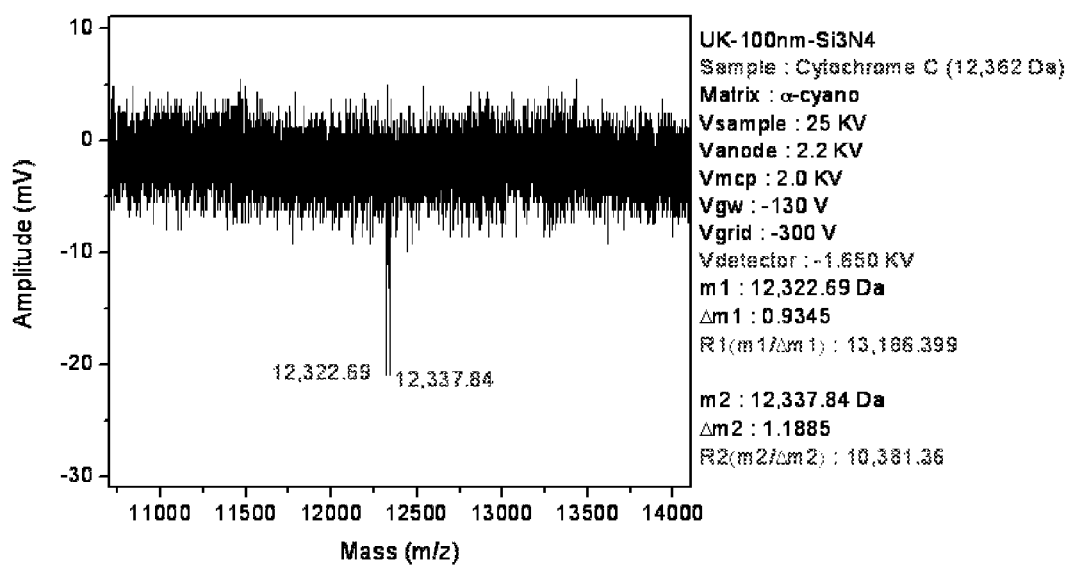
FIG. 10 shows a mass spectrum of cytochrome C (12,362 Da) obtained using a detector of the present invention.
Figure 11:
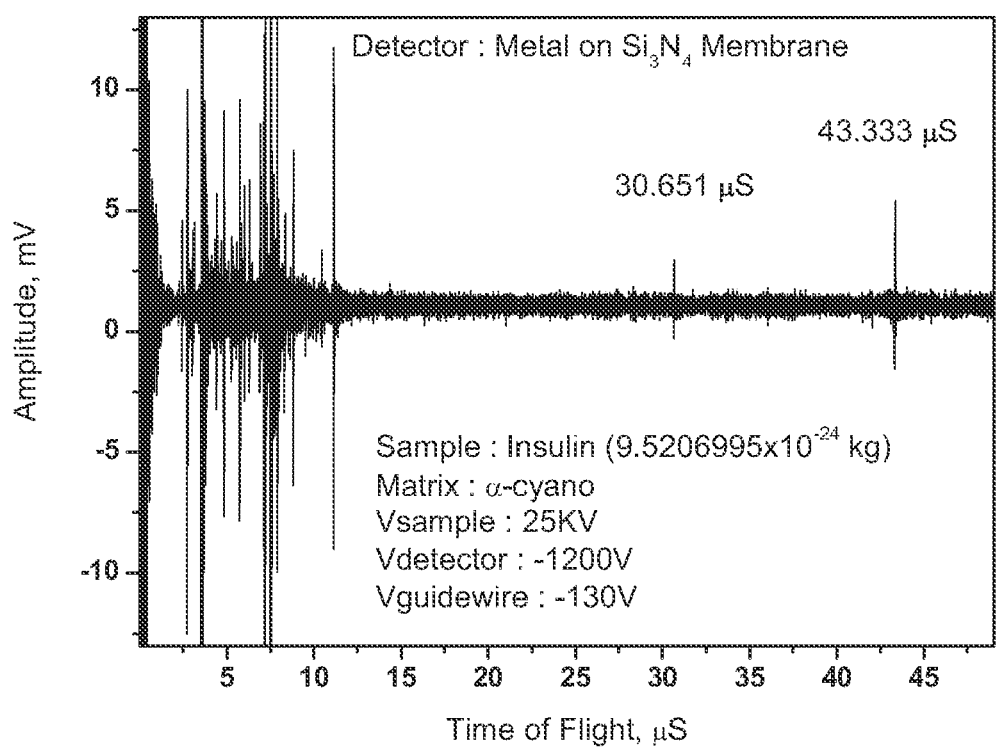
FIG. 11 shows a time of flight spectrum from insulin obtained using a detector of the present invention.

FIG. 7 shows a mass spectrum of angiotensin obtained using a detector of the present invention. Similarly, FIGS. 8 and 9 show a mass spectrum of bovine insulin obtained using a detector of the present invention, and FIG. 10 shows a mass spectrum of cytochrome C obtained using a detector of the present invention. FIG. 11 shows a time of flight spectrum from insulin obtained using a detector of the present invention. FIG. 9 shows the detector signal having less resolution (m/Δm=82.722) than as shown in other figures, however, even at lower resolution the detector is still able to detect the bovine insulin molecule. The membrane of FIG. 9 is partially broken so that the ions directly hit the detector. This figure serves as a comparison of the resolution and underlines the fact that in this low mass range the detector can still be effective. FIGS. 7, 8, and 10 show the true potential of the present invention with resolutions orders of magnitude better than the typical MALDI/TOF-MCP configuration (m/Δm greater than 2,500, 9,000 and 10,000). The two peaks shown in the figures are due to the two different longitudinal polarizations of acoustic phonons in the membrane. The relative peak distances increase with higher masses as expected for a linear dispersion relation of acoustic phonons.

The detection of proteins with this detector relies on the excitation of ballistic phonons by proteins hitting the membrane, which leads to phonon-assisted tunneling (PAT) so that electrons at the emitting layer are emitted into vacuum. These electrons are detected via an MCP and a fluorescent display, which enables real-time detection from a large scale membrane detector area. Semiconductor membranes made of silicon and silicon-nitride membranes constitute a passive membrane. Active gain is achieved, once the membrane is made of doped silicon, forming an embedded pn-junction, or using a membrane into which a heterostructure is embedded.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

One of ordinary skill in the art will appreciate that starting materials, reagents, purification methods, materials, substrates, device elements, analytical methods, assay methods, mixtures and combinations of components other than those specifically exemplified can be employed in the practice of the invention without resort to undue experimentation. AD art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

When a group of materials, compositions, components or compounds is disclosed herein, it is understood that all individual members of those groups and all subgroups thereof are disclosed separately. When a Markush group or other grouping is used herein, all individual members of the group and all combinations and subcombinations possible of the group are intended to be individually included in the disclosure. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. In the disclosure and the claims, "and/or" means additionally or alternatively. Moreover, any use of a term in the singular also encompasses plural forms.

All references cited herein are hereby incorporated by reference in their entirety to the extent that there is no inconsistency with the disclosure of this specification. Some references provided herein are incorporated by reference to provide details concerning sources of starting materials, additional starting materials, additional reagents, additional methods of synthesis, additional methods of analysis, additional biological materials, additional peptides, chemically modified peptides, additional cells, and additional uses of the invention. All headings used herein are for convenience only. All patents and publications mentioned in the specification are indicative of the levels of skill of those skilled in the art to which the invention pertains, and are herein incorporated by reference to the same extent as if each individual publication, patent or patent application was specifically and individually indicated to be incorporated by reference. References cited herein are incorporated by reference herein in their entirety to indicate the state of the art as of their publication or filing date and it is intended that this information can be employed herein, if needed, to exclude specific embodiments that are in the prior art, For example, when composition of matter are claimed, it should be understood that compounds known and available in the art prior to Applicant's invention, including compounds for which an enabling disclosure is provided in the references cited herein, are not intended to be included in the composition of matter claims herein.

The invention claimed is:

1. A detector for detecting molecules, said detector comprising:

a semiconductor membrane having an external surface for receiving said molecules, and an internal surface positioned opposite to said external surface, wherein said semiconductor membrane has a thickness of 5 nanometers to 50 microns;

an electron emitting layer comprising a material selected from the group consisting of metals, doped semiconductors and doped diamond materials provided on the internal surface of said semiconductor membrane, wherein said emitting layer is a single continuous layer on the internal surface of said semiconductor membrane having a thickness of 5 nanometers to 10 microns, wherein the device does not contain any nanopillars attached to said semiconductor membrane, and wherein said emitting layer emits electrons when said semiconductor membrane receives said molecules; and an electron detector positioned to detect at least a portion of said emitted electrons.

2. The detector of claim 1 wherein said emitting layer is electrically biased by applying a voltage of −3000 V to 3000 V to said emitting layer.

3. The detector of claim 1 wherein said emitting layer has a thickness of 5 nanometers to 25 nanometers.

4. The detector of claim 1 wherein said emitting layer is a metallic layer that conformally coats at least a portion of the internal surface of said semiconductor membrane.

5. The detector of claim 1 wherein said semiconductor membrane is provided at temperature of 2 K to 600 K.

6. The detector of claim 1 wherein said semiconductor membrane comprises one or more semiconductor materials selected from the group consisting of Si, Ge, SiN, diamond-on-insulator semiconductors, and combinations thereof.

7. The detector of claim 1 wherein said external surface of said semiconductor membrane is electrically biased by applying a voltage of −2000 V to 2000 V to said semiconductor membrane.

8. The detector of claim 1 wherein said semiconductor membrane comprises a plurality of layers of one or more semiconductor materials, wherein each of said layers have thicknesses of 1 nanometer to 1000 nanometers.

9. The detector of claim 1 further comprising a substrate having one or more active detector areas, wherein each active detector area comprises said semiconductor membrane and said emitting layer, wherein the semiconductor membrane of each active detector area has a surface area of 0.1 milimeters$^2$ to 20$^2$ centimeters$^2$.

10. The detector of claim 1 wherein said semiconductor membrane has a thickness of 50 nanometers to 300 nanometers.

11. The detector of claim 1 wherein said emitting layer is substantially flat having a thickness of 5 nanometers to 25 nanometers that does not vary by more than 5%.

12. The detector of claim 1 further comprising an electrode positioned between said inner surface of said membrane and said electron detector.

13. The detector of claim 12 wherein said electrode is a grid electrode electrically biased by applying a voltage of −2000 V to 2000 V to said electrode.

14. The detector of claim 1 wherein said semiconductor membrane further comprises a protective layer provided on the external surface, wherein said protective layer has a thickness of 5 nanometers to 25 nanometers.

15. The detector of claim 1 wherein said electron detector comprises one or more microchannel plate or dynode positioned in the path of electrons emitted by said emitting layer.

16. The detector of claim 15 wherein said electron detector further comprises a photoluminescent screen and photodetector, wherein said photoluminescent screen receives said electrons from said resonators and generates electromagnetic radiation which is detected by said photodetector.

17. The detector of claim 1 further comprising a mass analyzer selected from the group consisting of a quadrupole mass analyzer, magnetic sector mass analyzer, time of flight mass analyzer, and ion trap mass analyzer.

18. A method for detecting molecules comprising the steps of: providing a detector comprising:
   a semiconductor membrane having an external surface for receiving said molecules, and an internal surface positioned opposite to said external surface, wherein said semiconductor membrane has a thickness of 5 nanometers to 50 microns;
   an electron emitting layer comprising a material selected from the group consisting of metals, doped semiconductors and doped diamonds provided on the internal surface of said semiconductor membrane, wherein said emitting layer is a single continuous layer on the internal surface of said semiconductor membrane having a thickness of 5 nanometers to 10 microns, wherein the device does not contain any nanopillars attached to said semiconductor membrane, and wherein said emitting layer emits electrons when said semiconductor membrane receives said molecules;
   contacting said molecules with the external surface of said membrane, thereby generating electrons emitted by said emitting layer; and
   detecting the emitted electrons.

19. The method of claim 18 further comprising electrically biasing said emitting layer, said semiconductor layer or both so as to generate field emission, secondary electron emission or both from said emitting layer.

20. The method of claim 19 wherein said emitting layer is electrically biased using an at least partially transmissive grid electrode provided close enough to said emitting layer so as to establish an electric potential at said emitting layer selected over the range of −2000 V to 2000 V.

21. The method of claim 18 wherein said molecules are ions, said method further comprises accelerating said ions so as to impact said external surface having a kinetic energy equal to 10 to 50 keV.

22. The method of claim 18 wherein said molecules have a mass of at least 100 kDa.

23. The method of claim 18 wherein said method is carried out at a temperature of 2 K to 600 K.

24. The method of claim 18 wherein said step of detecting emitted electrons comprises the step of providing an electron detector in the path of at least a portion of said emitted electrons.

25. The method of claim 24 wherein said electron detector comprises a microchannel plate or a dynode.

26. The method of claim 18 wherein said step of detecting emitted electrons comprises amplifying said electrons from said emitting layer using a microchannel plate or dynode.

27. A method of detecting molecules comprising the steps of:
   a) providing a detector having active detector areas, wherein each active detector area comprises:
      a semiconductor membrane having an external surface for receiving said molecules, and an internal surface positioned opposite to said external surface, wherein said semiconductor membrane has a thickness of 5 nanometers to 50 microns;
      an electron emitting layer comprising a material selected from the group consisting of metals, doped semiconductors and doped diamonds provided on the internal surface of said semiconductor membrane, wherein said emitting layer is a single continuous layer on the internal surface of said semiconductor membrane having a thickness of 5 nanometers to 10 microns, wherein the device does not contain any nanopillars attached to said semiconductor membrane, and wherein said emitting layer emits electrons when said semiconductor membrane receives said molecules;
   b) contacting said molecules with the external surface of said semiconductor membrane;
   c) converting the kinetic energy of said molecules contacting the external surface into lattice vibrations of the semiconductor membrane to generate phonons;
   d) transferring said phonons to said emitting layer, thereby generating electrons from the emitting layer in response to said transfer of phonons; and
   e) detecting the electrons emitted by said emitting layer.

* * * * *

UNITED STATES PATENT AND TRADEMARK OFFICE
CERTIFICATE OF CORRECTION

PATENT NO. : 8,274,059 B2  Page 1 of 1
APPLICATION NO. : 12/489037
DATED : September 25, 2012
INVENTOR(S) : Robert H. Blick et al.

It is certified that error appears in the above-identified patent and that said Letters Patent is hereby corrected as shown below:

On the Title page at (75), replace:
            "Inventor: Robert H. Blick, Madison WI (US)"
    with :
            --Inventor:  Robert H. Blick, Madison WI (US);
                        Lloyd M. Smith, Madison WI (US);
                        Michael Westphall, Fichburg, WI (US);
                        Hua Qin, Suzhou (CN)--

Signed and Sealed this
Seventeenth Day of March, 2015

Michelle K. Lee
*Director of the United States Patent and Trademark Office*